(12) United States Patent
Ha et al.

(10) Patent No.: US 9,556,463 B2
(45) Date of Patent: Jan. 31, 2017

(54) GENES ENCODING BIOFILM FORMATION INHIBITORY PROTEINS AND A METHOD FOR PRODUCING L-LYSINE USING A BACTERIAL STRAIN WITH THE INACTIVATED GENES

(71) Applicant: CJ CHEILJEDANG CORPORATION, Seoul (KR)

(72) Inventors: Un Hwan Ha, Daejeon (KR); Yong Jae Kim, Seoul (KR); Jung Hoon Lee, Seoul (KR); Hee Sung Shin, Gyeonggi-do (KR); Jun Ok Moon, Seoul (KR); Hyung Joon Kim, Seoul (KR); Kwang Ho Lee, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 273 days.

(21) Appl. No.: 14/514,297

(22) Filed: Oct. 14, 2014

(65) Prior Publication Data

US 2015/0104837 A1     Apr. 16, 2015

(30) Foreign Application Priority Data

Oct. 15, 2013    (KR) ........................ 10-2013-0122443

(51) Int. Cl.
*C12N 1/20*      (2006.01)
*C07K 14/34*    (2006.01)
*C12P 13/08*     (2006.01)
*C12N 9/10*      (2006.01)
*C12N 9/06*      (2006.01)

(52) U.S. Cl.
CPC ................ *C12P 13/08* (2013.01); *C07K 14/34* (2013.01); *C12N 1/20* (2013.01); *C12N 9/0014* (2013.01); *C12N 9/1025* (2013.01); *C12Y 104/99001* (2013.01)

(58) Field of Classification Search
None
See application file for complete search history.

(56) References Cited

U.S. PATENT DOCUMENTS

2002/0106748 A1    8/2002   Mockel et al.

FOREIGN PATENT DOCUMENTS

| EP | 1 106 693 A1 | 6/2001 |
| EP | 1 108 790 B1 | 9/2009 |
| EP | 2 453 006 A2 | 5/2012 |
| WO | 2010/046221 A1 | 4/2010 |
| WO | 2012/008810 A2 | 1/2012 |

*Primary Examiner* — Suzanne M Noakes
*Assistant Examiner* — Jae W Lee (57) ABSTRACT

The present invention relates to a novel isolated gene (polynucleotide) which encodes a protein having a biofilm formation inhibitory activity derived from *Coryneform* bacteria, a L-lysine-producing strain in which the polynucleotide is inactivated, and a method for producing L-lysine using the same.

6 Claims, 5 Drawing Sheets

SEQUENCE LISTING

```
<160> NUMBER OF SEQ ID NOS: 15

<210> SEQ ID NO 1
<211> LENGTH: 1233
<212> TYPE: DNA
<213> ORGANISM: Corynebacterium glutamicum

<400> SEQUENCE: 1
atgagttcgt ctggaaaagt cattgttgtt ggagccggca tagtgggtct tgccaccgcc      60
tggcatttac aggagcacgg gttcgaggtg agcgtccttg atcgggatgg tgtcgctgca     120
ggttcttcgt ggggtaatgc tggttggtta gcgccggcga aaactattcc gttgtcggag     180
ccggggctgt ggacgtatgg tccgaaagag ctgttcaatc cggtgtcgcc gatgcatatg     240
ccacttcgtg tggatcccaa actgtggctt ttcttggcgc aatttatggc gcaggctttt     300
caacgcaagt gggattccac gatggcggac ctcacggaga tcgataaggt cgcgctcgaa     360
gcttttgatg aactgtcgat cggtggcgtg gaaggcctca cccatgaagg tccatttgtt     420
attggttttg aggaagagcg ccaatcggcg ggtttccgta aggaaattga tggcgtgagc     480
aggcacggcc agaaagtgga gatgtctcga ctggagaatc cacaagagtt ggcgccgatg     540
ctgaatgagc aaattcaggt ggcttaccgt ttggaaggcc agcgtttcat cgagccgggt     600
ccatacgtgc agtcattggc ggatgctgtg gtgaagcgtg gtggcgtgat ccgcgccggg     660
gcagaagttg tgcatgtggc gaagggtgat cgtcccgcgg tcattttggc ggatggtagc     720
cgtgaagaag cggacaaggt ggttgtggca acgggtgcct ggctgccggg tctaacgcgt     780
gaatacggtg tgaaaactct tgttcaggct ggtcgtggct attccttctc tgtggcaacg     840
gatattcctg ccaagcattc tgtgtaccct ccccaccacc gcatggcctg cacgccgtat     900
gagggccgtt tccgcattgc gggcaccatg gagttccgcg tccggatga gccgttccag     960 cagggccggg tggatgcgat tgtttcgcag gcgaagaagg ttatgagagg tattgatttc    1020
aacgatcgtc aggatgagtg ggtgggttcc cgcccggtca ctccggatgg gcgtccgttg    1080
attgggcaga ccaaggcgga gaacatttac gttgccggtg gtcacggcat gtggggtgtg    1140
gtgctgggcc ctgccaccgg taagtatttg gcggagctga tggctacggg caacaccaac    1200
ccgatcatca agccgttcga tccgctgcgt taa                                 1233

<210> SEQ ID NO 2
<211> LENGTH: 996
<212> TYPE: DNA
<213> ORGANISM: Corynebacterium glutamicum NCgl0350
```

<400> SEQUENCE: 2

```
atgactacat cgacggcaac tgctaaacaa caagcttcga aaagtcattt ccgtcccgac    60
attcaaggac tgcgagccgt cgcggtactt ttagtattga tatttcatgc tggcgatggc   120
tccgtgcttt ccggaggttt tacgggtgtt gatatttct ttgtaatttc tggctacttg   180
attactggac acttgatcag gtcttgtcta gaaaagggaa aaattagttt aattaacttt   240
tatgcgggcc ggattaggag aattctgcca gcagccacag ccgttttggt attcacggcc   300
ctaattacga ttttagtgtt gcctgatacc cggtggatgc ttatcggtgc tgagatcatt   360
gcaagttcag tgtatttggt aaactggctt tttgcctcaa atacgaatta tttgaatgca   420
gaagctgctg ccagtccagt tcagcattat ggaccttat ctgtggagga gcagttctat   480
atcctctggc cagcgctact tattgggttg ttgtatttca gtcggcatcg ttttacactg   540
gactcagagg aaactagtgg cacgaaacta acaaagttc gttggctgca gcgttatatc   600
gctttagcag ctgtacttat aacgttagtt tctctttgct tttccattta tttttcatac   660
accaatccgg cacccgcata tttcattacc tcgacacgcc tgtgggagct tggaataggc   720
gcgattctcg cctcttttc attccaatta gaacgaattt cagctccgat aggatatgcg   780
cttggtgtaa tgggattagc aagcatcgta gcagctggag tgactttga ttctcagaca   840
gttttcccg gctatgccgc gctggtgcca acattaggtg cagcagctgt aattattggt   900
ggcatgggag gtcgtgcgga aaaggtgta ggtgtacttc taaaagttaa acctatgcgt   960
tggatcggag atctttccta ttcgctttat ctatag                            996
```

<210> SEQ ID NO 3
<211> LENGTH: 1989
<212> TYPE: DNA
<213> ORGANISM: Pseudomonas aeruginosa PA5238

<400> SEQUENCE: 3

```
atgtcgagcc tgccttatcg aagagatatc gatggattgc gcgcactggc catcttgtcg    60
gtggtgttct atcacttggg cttgggcggt ttcaccggcg ggtatgtcgg cgtcgatgtc   120
tttctggtga tttccggcta cctgatcact tcgatcatcc ggcgcgatcg gcaggccggg   180
cgtttcagct tcgtcgattt ctgggctcgc cgggcgcgac gcatcctccc cgctttgttc   240
gttatgatgg ccgtcagcct ggcggccggc tggttcctga tggagccgcg ggactacgag   300
caattgggtc gttcggtgcg ttaccagacg atgttcgcct cgaacatcct gttctggaag   360
caggatggct atttcgacgc gcgtccgaa ttcaagccgc tattgcatac ctggtcgttg   420
tcggtggaag agcagttcta cattctcttc ccgctactgc tggccgcgat ctccgggcgc   480
ctgctgcgct ggcggctcgc catcctcctc gcggtcctgg cgctatcgct ggcggccagc   540
gtctgggcgg tgagccagcg acctggcagt gcattcttcc tcctgccgat gcgcgcctgg   600
gaactcctgg cgggtgccgc gctggcgttg ctgccgggcg ctagccgcgg tcattcgcag   660
tggtccctgc aactggcggc caccctcggc atagcggcga ttctcctgcc ggtgttcttc   720
tacgacagcg acactccttt ccccggcctc gcggcgctgc cggcggtgct ggcaccgcc   780
ctgctgatct gggccaacgg cgccggcgac acctgggttc gccgcctgct gggctggcaa   840
ccgctggtct ggttcggtct gatctcctat tcgctgtacc tctggcactg gccgctgtac   900
gtcttcgtcc agtaccacgc actggaaacc ctgggcctgc cggcacgcct ggggttgctg   960
gcggcgagca tcggcctggc ggcactgtcg ctgtactacg tcgaggcacc gttccgcgag  1020
```

```
cgcaagctgt tcgccgggcg ccggcagatg cttggcgcgg cgctgtgcag cttgctgctg    1080
ctgggagtca tcggccagtt ggtgcggcat tacgacggcg tgccgtcgcg tctttccgag    1140
gaagccttgc gttatgccaa ggcgtccaaa tggcgcgatg ggcagaccga ctgcatgttc    1200
gacaagaagg cgctcagtca ggaaagcatc tgccgcttcc cggcggaact ggctgccgaa    1260
cgaccgctgc tggtcagttg gggcgacagc cattccgcgg cgttgagccc gctgctgcgc    1320
gaactggcta ccagtcgccg actgccgatc tggcaggctt cgctggcggg ctgtccgccg    1380
ttgctgggga tgctggaaaa ggacacttgc ctgcgtttca accagcagat gctcgagttc    1440
gtcgaacagc agcggccggg cggggtgatc ctcgccgggc gctgggacat gtatatatac    1500
ggcgactcgc aggacggtac ccgcaacatt ctccgcgagc cggacgacac gccggacagc    1560
tcgatcgccg aggcgctgct gcggcaacgc ctgagcggga tgatcgaaag ctgaacgcg     1620 gccgacgtac atgtctggct ggtcaaggac gtaccgctgc tgccattcaa ggcaccggcg    1680
cggctggtgc ggctgagtct gagcggggag gatgtcgggc gcgcacgttt tcccttcgct    1740
gagcacgctg cgcgcgtcgc ctacgtgaat gcgctgttcg atgcgttggc cgaaggcaac    1800 ccgcggggtga gcgtgctcga cccctccagc gtgctctgcg atggcctgga ttgtttcgcc    1860
gaacgtgatg gctggtcact gtacatggat aacaaccacc tttcgaccca gggggcccat    1920
gaactcgggc ctttgttcga gccgatgcta cagagcctcg acgactcgag gatcgccagc    1980
cagcagtga                                                            1989

<210> SEQ ID NO 4
<211> LENGTH: 1320
<212> TYPE: DNA
<213> ORGANISM: Pseudomonas aeruginosa PA5309

<400> SEQUENCE: 4
atgaacgccc gcgttcacca gccggtgcat accgcccaac acgccccctc ctactacgcc      60
gccacgctca accgacgcat cgagtgccct cccctggccg gcgaagaaca ggccgacgtg     120
tgcgtcgtcg gcggcggctt ctcgggagtg aacacggcgt tggaactggc ccagcgcggc     180
ttctccgtgg tcctgctgga agcgcaccag atcggctggg gcgccagtgg acgcaatggc     240
ggccagttga tccgcggcgt cggccatgac gtcgagcagt tcctcccggt gatcggcgcc     300
gacggcgtga aggcactcaa gctgatgggc ctggaggcgg tggagatcgt ccgtcgccgg     360
gtcgagcagt acgccatcga ctgcgatctg cgctggggct actgcgacct ggcgaacaag     420
cccggcgact accagggctt ccgcgaggac atggaggaac tccaggccct cggctatcgc     480
cacgagatgc gcctggtgcc ggccgcggag atgcgcagcg tgatcggctc cgatcgctac     540
gtcggcggcc tggtggacat gggctctggc cacctgcacc cgctcaacct ggtcctcggc     600
gaagccgccg ctgcccagtc gctgggcgtc cgcctgttcg agcgctcgac ggtgatgcgg     660
atcgactacg gcacggaagt ccaggtgcat accgccaccg gcaaagtgcg ggcgaagacc     720
ctggtgctgg gctgcaacgc ctacatgaac gacctcaacc cgctgctcgg cggcaaggta     780
ctgccggccg gcagctacgt gatcgccacc gaaccgctgg acgagaaact ggcccgccaa     840
ctgctgccga gaacatggcc ggtgtgcgac cagcgcgtgg ccctcgacta ctaccggctc     900
tccgccgaca accgcctgct gttcggtggc gcctgccatt attccggccg cgaccccagc     960
gacatcgccc cctacatgcg gccgaagatg ctggaggtat tccgcaact ggcgaacgtc     1020 cgcatcgact accaatgggg cggcatgatc ggcatcggcg ccaatcgcct gccacagatc    1080
ggccgcctgc cggggcagcc caacgtgtac ttcgcccagg cctattccgg acacggggtg    1140
```
aacgccacgc acctcgccgg gcagttgctc gccgaagcca tcggcggcca gcagagcgac    1200
ggcttcgacc tgttcgccaa ggtgccgcac atcaccttcc ccggcggcaa gctgctgcgc    1260
tcgccactgc tggcgctggg catggcctgg taccggctga aggaaaaact cggtagctga    1320

<210> SEQ ID NO 5
<211> LENGTH: 27
<212> TYPE: DNA
<213> ORGANISM: Artificial Sequence
<220> FEATURE:
<223> OTHER INFORMATION: Primer(PA5238F)

<400> SEQUENCE: 5
gtggtcatcc tgctcgactc catcacc                                          27

<210> SEQ ID NO 6
<211> LENGTH: 27
<212> TYPE: DNA
<213> ORGANISM: Artificial Sequence
<220> FEATURE:
<223> OTHER INFORMATION: Primer(PA5238R)

<400> SEQUENCE: 6
cgaggcgaac atcgtctggt aacgcac                                          27

<210> SEQ ID NO 7
<211> LENGTH: 895
<212> TYPE: DNA
<213> ORGANISM: Pseudomonas aeruginosa

<400> SEQUENCE: 7
gtggtcatcc tgctcgactc catcacccgt ctggcgcggg cctacaacac cgtgatcccc      60
agctccggca aggtgctcac cggcggtgtc gacgcccatg ccctggagaa gccgaagcgc     120
ttcttcggcg ccgcgcggaa catcgaagag ggcggttctc ttacgattct cgccacggcg     180
ttggtggaaa ccgctcgaa gatggacgag gtgatctacg aggaattcaa gggtaccggc     240
aacatggaac tcccattgga tcgcaagatc gccgagaagc gcgtgttccc ggccatcaac     300
atcaaccgtt cgggtacccg ccgcgaagag ctgctgacca gcgaggacga gctccagcgc     360
atgtggatcc tgcgcaagat cctgcacccg atggacgaga tctccgcgat cgaattcctc     420
atcgacaagc tcaagcagac caagaccaac gatgagttct tcgattcgat gaaacggaag     480
tagtcttcca gggaattgaa gaaggcgctc cggtttgacc ggagcgcctt ttttcatgcc     540
tggagaaaaa tagatgtcga gcctgcctta tcgaagagat atcgatggat tgcgcgcact     600
ggccatcttg tcgtggtgt tctatcactt gggcttgggc ggtttcaccg gcgggtatgt     660
cggcgtcgat gtcttctgg tgatttccgg ctacctgatc acttcgatca tccgcgcgca     720
tcggcaggcc gggcgtttca gcttcgtcga tttctgggct cgccgggcgc gacgcatcct     780
ccccgctttg ttcgttatga tggccgtcag cctggcggcc ggctggttcc tgatggagcc     840
gcgggactac gagcaattgg gtcgttcggt gcgttaccag acgatgttcg cctcg         895

<210> SEQ ID NO 8
<211> LENGTH: 25
<212> TYPE: DNA
<213> ORGANISM: Artificial Sequence
<220> FEATURE:
<223> OTHER INFORMATION: Primer(2909F1)

<400> SEQUENCE: 8
gctctagact ctagcccaag cactc	25

<210> SEQ ID NO 9
<211> LENGTH: 32
<212> TYPE: DNA
<213> ORGANISM: Artificial Sequence
<220> FEATURE:
<223> OTHER INFORMATION: Primer(2909R1)

<400> SEQUENCE: 9
acggccctca tacggcacac gaagtggcat at	32

<210> SEQ ID NO 10
<211> LENGTH: 32
<212> TYPE: DNA
<213> ORGANISM: Artificial Sequence
<220> FEATURE:
<223> OTHER INFORMATION: Primer(2909F2)

<400> SEQUENCE: 10
atgccacttc gtgtgccgta tgagggccgt tt	32

<210> SEQ ID NO 11
<211> LENGTH: 25
<212> TYPE: DNA
<213> ORGANISM: Artificial Sequence
<220> FEATURE:
<223> OTHER INFORMATION: Primer(2909R2)

<400> SEQUENCE: 11
gctctagaac cttgtactgc gccga	25

<210> SEQ ID NO 12
<211> LENGTH: 35
<212> TYPE: DNA
<213> ORGANISM: Artificial Sequence
<220> FEATURE:
<223> OTHER INFORMATION: Primer(0350F1)

<400> SEQUENCE: 12
cgactctaga ttaggtctta gttgccatga tcggt	35

<210> SEQ ID NO 13
<211> LENGTH: 33
<212> TYPE: DNA
<213> ORGANISM: Artificial Sequence
<220> FEATURE:
<223> OTHER INFORMATION: Primer(0350R1)

<400> SEQUENCE: 13
tgcacctaat gttggccatc gccagcatga aat	33

<210> SEQ ID NO 14
<211> LENGTH: 33
<212> TYPE: DNA
<213> ORGANISM: Artificial Sequence
<220> FEATURE:
<223> OTHER INFORMATION: Primer(0350F2)

<400> SEQUENCE: 14
tcatgctggc gatggccaac attaggtgca gca	33

<210> SEQ ID NO 15
<211> LENGTH: 33
<212> TYPE: DNA
<213> ORGANISM: Artificial Sequence

```
<220> FEATURE:
<223> OTHER INFORMATION: Primer(0350R2)

<400> SEQUENCE: 15
atctctagag cagcttggct tctatttgga gat                                33
```

GENES ENCODING BIOFILM FORMATION INHIBITORY PROTEINS AND A METHOD FOR PRODUCING L-LYSINE USING A BACTERIAL STRAIN WITH THE INACTIVATED GENES

CROSS REFERENCE TO RELATED APPLICATION

This application claims priority to Korean Patent Application No. 10-2013-0122443, filed Oct. 15, 2013, which application is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_033_00US_ST25.txt. The text file is 12 KB, was created on Dec. 16, 2014, and is being submitted electronically via EFS-Web.

BACKGROUND OF THE INVENTION

1. Field of the Invention

The present invention relates to a novel isolated genes which encode a protein having a biofilm formation inhibitory activity, and a method for producing L-lysine by using a bacterial strain in which the gene is inactivated.

2. Description of the Related Art

Bacteria compete with other microorganisms for nutrients while growing under various growth conditions. When the growth conditions for bacteria become unfavorable and threaten theft survival, the bacteria utilize various survival mechanisms including biofilm formation.

Biofilms are assemblages of microorganisms encased within a self-produced matrix of extracellular polymers, which functions as a cooperative consortium. Biofilms serve as protection barriers and enable bacteria to survive as communities in biofilms in inhospitable conditions such as antibiotics treatments, host immune responses, and antibacterial agents.

Reportedly, as the mass of bacteria increases, the L-lysine production yield decreases. Thus, there is a problem that L-lysine production yield depends on changes in bacterial mass.

After numerous experiments, the inventors of the present invention have succeeded in identifying a gene related to inhibition of biofilm formation in a L-lysine-producing bacterial strain. They have also found that the growth rate of the strain can be increased by the inactivation of the gene, leading to an increase in the mass of the bacteria. Unexpectedly, they have also found that the yield of L-lysine production does not decrease at all despite the increase in the bacterial mass, thereby completing the present invention.

SUMMARY OF THE INVENTION

An object regarding to the present invention is to provide a novel isolated genes which encode a protein having a biofilm formation inhibitory activity in a L-lysine-producing strain, a L-lysine-producing strain in which the gene is inactivated, and a method for producing L-lysine by using the L-lysine-producing strain having the inactivated gene.

BRIEF DESCRIPTION OF THE DRAWINGS

FIG. 2 panel A shows a process preparing pHS1004 vector for measuring expression level of the promoter of *Pseudomonas aeruginosa* PA5238 which is similar to NCgI0350 gene, which the pHS1004 vector was prepared by linking the promoter of PA5238 to upstream of promoterless lacZ gene of pD19lacΩ vector.

FIG. 2 panel B shows that the promoter expression of PA5238 was induced in proportion to concentration of the cell-free culture broth. The cell-free culture broth was obtained from the cultured solution in a stationary phase, in which *Pseudomonas aeruginosa* was transduced with the pHS1004 vector.

FIG. 2 panel C shows the treatment time of the cell-free culture broth required for measuring PA5238 gene expression in *Pseudomonas aeruginosa* transduced with the pHS1004 vector.

DETAILED DESCRIPTION OF THE PREFERRED EMBODIMENTS

An embodiment of the present invention provides a novel isolated polynucleotide (NCgI2909) which encodes a protein having an inhibitory activity against bacterial biofilm formation, represented by a nucleotide sequence of SEQ ID NO: 1, or a polynucleotide which encodes a protein having an activity equivalent thereto.

The polynucleotide (NCgl2909) represented by SEQ ID NO: 1 is a gene encoding a D-amino acid dehydrogenase subunit in *Coryneform* bacteria, and is located in upstream of an acyltransferase gene (NCgl0350) represented by nucleotide sequence of SEQ ID NO: 2. The polynucleotide (NCgl2909) regulates expression of the acyltransferase gene (NCgl0350) and a promoter thereof. In particular, the polynucleotide (NCgl2909) represented by SEQ ID NO: 1 inhibits biofilm formation by expressing the acyltransferase gene in the presence of a cell-free culture broth of bacteria grown to a stationary phase.

As used herein, the term "a gene(polynucleotide) which encodes a protein having a biofilm formation inhibitory activity" refers to a gene which encodes a protein involved in the inhibition mechanism of biofilm formation. In addition, the genes could be included; a gene inhibiting the expression of a gene encoding a substance required for biofilm formation, a gene encoding a substance required for cell dispersion from the biofilm, a gene encoding a protein involved in the regulation to induce the gene expression or modification of extracellular or intracellular metabolites accompanied by the biofilm formation.

As used herein, the term "polynucleotide which encodes a protein having an activity equivalent" includes a functional equivalent thereof, as long as it maintains the activity of a protein encoded by the polynucleotide, and may include variants prepared by deletion, substitution, insertion or combination thereof of a partial nucleotide sequence of the polynucleotide or by artificial modification, or a functional fragment of the polynucleotide which performs the same action.

As used herein, the term "*Coryneform* bacteria" include microorganisms belonging to the genus *Corynebacterium* or *Brevibacterium*. The *Coryneform* bacteria may include *Corynebacterium glutamicum* other wild-type strains known as suitable strains of the genus *Corynebacterium*, *Corynebacterium ammoniagenes*, *Corynebacterium thermoaminogenes* (*C. thermoaminogenes*), *Brevibacterium flavum* and *Brevibacterium lactofermentum* (*B. lactofermentum*), and L-amino acid-producing mutants or strains prepared therefrom. For example, the bacteria could be *Corynebacterium glutamicum* KCCM11016P and *Corynebacterium glutamicum* KCCM10770P, but are not limited thereto.

Specifically, the bacteria may be at least one selected from the group consisting of *Corynebacterium glutamicum*, *Corynebacterium ammoniagenes*, and *Corynebacterium thermoaminogenes* among the coryneform bacteria.

More specifically, the bacteria may be bacteria with improved L-lysine productivity among *Coryneform* bacteria, in which one or more genes related to lysine biosynthesis are enhanced.

As used herein, the term "cell-free culture broth" refers to a culture broth prepared by culturing the bacteria up to a stationary phase, centrifuging the culture solution, and passing the supernatant through a filter such as a cellulose acetate filter to remove the bacteria.

The cell-free culture broth includes cell-free culture broths of Gram-positive and Gram-negative bacteria. Specifically, as the cell-free culture broth of bacteria, the bacteria may be selected from the group consisting of *Escherichia coli*, *Pseudomonas aeruginosa*, *Salmonella typhimurium*, *Bacillus subtilisBacillus subtilis*, *Corynebacterium ammoniagenes*, *Corynebacterium glutamicum*, *Mycobacterium smegmatis*, *Mycobacterium sp. strain JC*1, and *Staphylococcus aureus*.

As used herein, the term "stationary phase" refers to a point at which the bacteria not grow anymore after the bacterial growth reaches a certain level.

The cell-free culture broth of the bacteria cultured to the stationary phase includes an autoinducer as a mediator of quorum sensing.

As used herein, the term "autoinducer" refers to a mediator of quorum sensing, that is, a particular molecule synthesized by bacteria for signaling in response to environmental change between cells exported or imported for communication. The autoinducer includes acylhomoserine lactone-based, peptide-based, and furanone-based autoinducers.

Further, an embodiment of the present invention provides *Coryneform* bacteria in which NCgl2909 (SEQ ID NO: 1) gene, NCgl0350 (SEQ ID NO: 2) gene, or NCgl2909 and NCgl0350 gene which encodes a protein having an inhibitory activity against bacterial biofilm formation is/are inactivated Specifically, the *Coryneform* bacteria may be at least one selected from the group consisting of *Corynebacterium glutamicum*, *Corynebacterium ammoniagenes*, and *Corynebacterium thermoaminogenes*.

More specifically, the *Coryneform* bacteria may be any bacteria among the *Coryneform* bacteria with improved L-lysine productivity, in which one or more gene related to lysine biosynthesis are enhanced.

The gene related to lysine biosynthesis may include lsyA (gene encoding diaminopimelate decarboxylase), lysC (gene encoding aspartate kinase), lysE (gene encoding lysine export carrier), dapA (gene encoding dihydrodipicolinate synthase), dapB (gene encoding dihydrodipicolinate reductase), pyc (gene encoding pyruvate carboxylase), asd (gene encoding aspartate semialdehyde dehydrogenase), aspB (gene encoding aspartate aminotransferase) or the like. The bacteria, where the gene related to lysine biosynthesis is enhanced, may be *Coryneform* bacteria with improved L-lysine productivity by enhancing activities of the enzymes encoded by one or more genes selected from the genes related to lysine biosynthesis.

Activities of the enzymes encoded by the genes may be enhanced by increasing copy number of the gene, by replacing or modifying an expression control sequence of the gene, or by introducing a mutation into ORF. The increase in the copy number of the gene may include the increase in the copy number by introduction of an exogenous gene as well as additional introduction of the endogenous gene. The replacement or modification of the expression control sequence of the gene may be insertion of a exogenous strong promoter to upstream of the start codon of the gene, or introduction of a mutation for enhancement of the promoter activity, or introduction of a mutation for efficient operation of SD sequence. The introduction of a mutation into ORF of the gene may be performed by using one or more methods selected from the group consisting of deletion, substitution, and insertion of a part of the nucleotide sequence. The insertion, deletion and substitution of a nucleotide sequence in the chromosome of the gene may be performed by any method known in the art, for example, homologous recombination.

Examples of the *Coryneform* bacteria with improved L-lysine productivity by enhancing activities of the enzymes encoded by the genes may include *Corynebacterium glutamicum* KCCM10770P strain prepared by insertion of two copies of aspB, lysC, asd, dapA, dapB and lysA genes into *Corynebacterium glutamicum* KCCM11016P, which is a lysine-producing strain prepared by artificial mutation using the wild-type *Corynebacterium glutamicum* ATCC13032 as a parent strain, or *Corynebacterium glutamicum* KCCM11016P-CJ5 strain prepared by insertion of two copies of aspB, lysC, asd, dapA, dapB, lysA and pyc genes thereto. It was confirmed that *Corynebacterium glutamicum* KCCM10770P showed an approximately 7% increase in L-lysine production, compared to the lysine-producing strain, *Corynebacterium glutamicum* KCCM11016P, and *Corynebacterium glutamicum* KCCM11016P-CJ5 showed an approximately 8% increase in L-lysine production, compared to *Corynebacterium glutamicum* KCCM11016P (Korean Patent No. 10-0924065).

Further, the *Coryneform* bacteria with improved L-lysine productivity may be a lysine-producing strain, *Corynebacterium glutamicum* KFCC10750 (Korean Patent No. 10-0073610) (Accession No. KCCM11347) prepared by artificial mutation using ATCC13032 as a parent strain, *Corynebacterium glutamicum* CJ3P having an ability to produce L-lysine, which is prepared by introducing the known mutations of pyc(P458S), hom(V59A), lysC(T311I) into three types of genes using ATCC13032 as a parent strain (Binder et al. Genome Biology 2.012, 13:R40), or *Corynebacterium glutamicum* KCCM 11085P with improved L-lysine productivity which is prepared by increasing NADPH production in the pentose phosphate pathway through attenuation of gluconate kinase activity (Korean Patent Laid-open Publication No. 10-2012-0007965).

As used herein, the term "inactivation of a gene" refers to reduction or elimination in the activity of the protein encoded by a gene due to the reduction or elimination of the gene expression via mutation induced by one or more methods selected from the group consisting of deletion of all or a part of the corresponding gene, substitution of a part of the nucleotide sequence, or insertion of one or more base pairs into the nucleotide sequence.

As an embodiment of the present invention, a recombinant vector including a part of NCgI2909 (SEQ ID NO: 1) or NCgI0350 (SEQ ID NO: 2), or NCgI2909 and NCgI0350 gene(s) is/are introduced into a microorganism to induce inactivation of the endogenous gene, thereby preparing a microorganism in which a biofilm synthesis inhibitory mechanism is inhibited.

In detail, the microorganism may he prepared by a method including: 1) obtaining a polynucleotide fragment containing a part of both ends of the gene; 2) constructing a recombinant vector by introducing the obtained polynucleotide fragment into the vector capable of performing homologous recombination in the chromosome of host cells; 3) preparing homologous recombinants by introducing the obtained recombinant vector into host cells capable of producing L-lysine; and 4) selecting a strain, in which NCgI2909 or NCgI0350, or NCgI2909 and NCgI0350 gene(s) is/are inactivated, from the homologous recombinants.

The vector to be used may include a pDZ vector, pBR-based, pUC-based, pBluescriptII-based, pGEM-based, pTZ-based, pCL-based and pET-based vectors, but is not limited thereto. Specifically, the above genes may be inactivated using a pDZ vector (Korean Patent No. 10-0924065) which is not autoreplicable in *Corynebacterium glutamicum*

In the present invention, a pDZ derivative including a part of the gene encoding NCgI2909 was prepared, based on the pDZ vector. The pDZ derivative was named as pDZ-ΔNCgI2909, and transformed into a *Corynebacterium glutamicum* strain to prepare a recombinant strain, in which the NCgI2909 gene was inactivated. The recombinant strain was named as ATCC13032:ΔNCgI2909 or KCCM11016P::ΔNCgI2909. Similarly, a pDZ derivative including a part of the NCgI0350 gene was prepared, and named as pDZ-ΔNCgI0350. The pDZ-ΔNCgI0350 was transformed into a *Corynebacterium glutamicum* strain to prepare a recombinant strain, in which the NCgI0350 gene was eliminated. The recombinant strain was named as KCCM11016P::ΔNCgI0350. Furthermore, KCCM11016P:ΔNCgI2909 was transformed with a recombinant plasmid pDZ-ΔNCgI0350 to prepare a strain, in which both genes encoding NCgI2909 and NCgI0350 were inactivated, and the strain was named as CA01-2270 (KCCM11016P::ΔNCgI2909ΔNCgI0350).

The *Corynebacterium glutamicum* ATCC13032: ΔNCgI2909 of the present invention showed 4~5-fold increased biofilm-forming ability, compared to the wild-type. Further, the coryneform bacterium, in which NCgI2909 or NCgI0350 gene, or NCgI2909 and NCgI0350 gene(s) is/are inactivated, is characterized in that L-lysine production is not reduced, even though the mass of the bacteria increased, unlike the conventional L-lysine-producing *Coryneform* bacteria.

In addition, an embodiment of the present invention provides a method for producing L-lysine by using the coryneform bacterium, in which NCgI2909 or NCgI0350 gene, or NCgI2909 and NCgI0350 gene(s) is/are inactivated.

The method for producing L-lysine includes culturing the coryneform bacterium, in which NCgI2909 or NCgI0350 gene, or NCgI2909 and NCgI0350 gene(s) is/are inactivated in a culture solution; and recovering L-lysine from the cultured bacteria or the culture solution thereof.

The method for culturing the coryneform bacterium, in which NCgI2909 or NCgI0350 gene, or NCgI2909 and NCgI0350 gene(s) is/are inactivated, may be performed by a method widely known in the art. Specifically, a batch, a fed-batch or a repeated a led batch process may be used in a continuous manner, but the present invention is not limited thereto.

For use in the cultivation a medium, that is a culture solution, must satisfy the requirement of a particular strain. Culture solution for *Corynebacterium* strain is well known (e.g., Manual of Methods for General Bacteriology. American Society for Microbiology, Washington D.C., USA, 1981). Carbon sources to be used may include saccharides and carbohydrates such as glucose, sucrose, lactose, fructose, maltose, starch and cellulose; oils and lipids such as soybean oil, sunflower seed oil, castor oil and coconut oil; fatty acids such as palmitic acid, stearic acid, linoleic acid; alcohols such as glycerol and ethanol; and organic acids such as acetic acid. These materials may be used separately or in combination. Nitrogen sources to be used may include peptone, yeast extract, meat broth, malt extract, corn steep liquor, soybean meal and urea, or inorganic compounds, for example, ammonium sulfate, ammonium chloride, ammonium phosphate, ammonium carbonate and ammonium nitrate. The nitrogen sources may be used separately or in combination. Phosphorus sources to be used may include dipotassium hydrogen phosphate, potassium dihydrogen phosphate, and corresponding sodium-containing salts. In addition, culture solution may contain metal salts such as magnesium sulfate or iron sulfate required for the growth. Lastly, essential nutrients such as amino acids and vitamins may be additionally used. In addition, proper precursors may he added to the culture solution. These materials may he properly added to the culture during cultivations in a batch or continuous mode. However the present invention is not limited thereto The pH of the culture solution may be adjusted with a basic compound such as sodium hydroxide, potassium hydroxide or ammonia, or an acidic compound such as phosphoric acid or sulfuric acid. The generation of foam may he restrained using an anti-foaming agent such as fatty acid polyglycol ester. The culture solution may be kept under aerobic conditions by introducing oxygen or an oxygen-containing gas (e.g., air) thereto. The culture temperature is typically between 20° C. and 45° C. and specifically between 25° C. and 40° C. The culturing is continued until a maximal amount of L-lysine is produced. In this regard, it may be accomplished within 10 to 160 hrs. Upon production, L-lysine may be exported into the culture media or may be remained within the cells.

The method of recovering L-lysine from the microorganism or the culture solution is widely known in the art. Examples of the L-lysine recovering method may include filtration, anion exchange chromatography, crystallization and HPLC, but are not limited thereto.

The inventors of the present invention have selected a polynucleotide PA5238 (SEQ ID NO: 3) in *Pseudomonas aeruginosa*, based on the polynucleotide NCgl9350 which is regulated by an autoinducer secreted from coryneform bacterium disclosed in Korean Granted Patent No 10-1134700 previously filed by the present inventors. Additionally, they have searched polynucleotides, which is located upstream of PA5238 and functions as regulator, and selected a polynucleotide PA5309 (SEQ ID NO: 4). Additionally, based on PA5309, they have selected a similar polynucleotide NCgl2909 (SEQ ID NO: 1) in *Coryneform* bacteria.

Thereafter, the wild-type strains having the selected genes represented by SEQ ID NOS: 1 to 4 and mutant strains having the inactivated genes were prepared, respectively. The examined effects on biofilm formation confirmed that the mutant strains showed approximately 4 times higher biofilm formation than the wild-type strains having the genes of SEQ ID NOS: 1 to 4.

Therefore, it was confirmed that the genes represented by SEQ ID NOS: 1 to 4 may inhibit biofilm formation or be involved in the inhibition mechanism of biofilm formation.

Further, the present inventors examined L-lysine producibility according to proliferation of the lysine producing strain, in which the gene represented by SEQ ID NO: 1 or 2, or the genes represented by SEQ ID NOS: 1 and 2 is/are inactivated. As a result, its L-lysine production yield was not reduced, whereas the L-lysine production yield is generally reduced with increasing mass of bacteria. Therefore, it was confirmed that a large amount of L-lysine can be produced in a short period of time using this strain, compared to the conventional strain.

Hereinafter, the present invention will be described in more detail with reference to Examples. However, these Examples are for illustrative purposes only, and they should not be interpreted as limiting the scope of the present invention.

EXAMPLE 1

Induction of Expression of Acyltransferase Gene (NCgI0350) Promoter of *Coryneform* Bacteria in Presence of Cell-Free Culture Broths Obtained from Various Bacteria <1-1> Cell Cultivation in Presence of Cell-Free Culture Broth

*Corynebacterium glutamicum* ATCC13032 and *Corynebacterium ammoniagenes* were cultured with shaking in MB medium (0.4% yeast extract; 1% tryptone; 0.4% soytone; and 0.5% NaCl: all w/v) at 30° C. for 36 hours.

*Agrobacterium tumefaciens, Escherichia coli, Bacillus subtilisBacillus subtilis, Mycobacterium smegmatis, Mycobacterium* sp. strain JC1, *Pseudomonas aeruginosa, Staphylococcus aureus, Bacillus subtilisStreptomyces natalensis* and *Salmonella typhimurium* were cultured with shaking in LB medium (0.5% yeast extract; 1% tryptone; and 1% NaCl; all w/v) at 37° C. for 36 hours.

*Vibbrio harveyi* was cultured with shaking in LB medium containing 3% NaCl at 37° C. for 36 hours.

The culture solutions of 11 types of the strains except *Corynebacterium glutamicum* ATCC13032 were centrifuged at 10,000×g for 10 minutes, and then each supernatant was passed through a cellulose acetate filter (0.2 µm) to prepare each cell-free culture broth of the strains.

The *Corynebacterium glutamicum* ATCC13032 was recovered from the culture solution of it, which cultured until $OD_{600}$ reached 1.3 in the same manner, and then suspended in MB medium prepared by mixing the each cell-free culture broth and a fresh medium at a ratio of 1:1, and cultured further at 30° C. for 24 hours.

<1-2> Induction of Expression of Acyltransferase Gene Promoter in Presence of Cell-Free Culture Broths In order to examine expression of the promoter of the NCgI0350 gene in presence of the cell-free culture broth, the present inventors used a method (herein, referred to as 'growth permissive assay') suggested in the granted Korean Patent No. 10-1134700.

This method will he described in more detail as follows.

The promoter region (SEQ ID NO: 1 of the grated Korean Patent No. 10-1134700) of NCgI0350 gene of *Corynebacterium glutamicum* ATCC13032 was amplified. This amplified promoter region was inserted into a T&A vector (Real Biotech Corporation), and then digested with PstI and cloned into a pSK1CAT vector which had digested with the same enzyme, so as to prepare a pHS09004 vector where the promoter region of NCgI0350 was inserted, The pSK1CA T vector used in the preparation of the pHS09004 vector is a promoterless vector including cat gene, encoding chloramphenicol acetyltransferase providing chloramphenicol resistance in Gram-positive bacteria.

The pSK1CAT vector and pHS09004 vector were transformed into the wild-type *Corynebacterium glutamicum* ATCC13032 respectively, and C3 and C6(P0350:CAT) transformant strains were prepared, respectively.

The C3 and C6 transformant strains were cultured in MB media containing 30 µg/ml of kanamycin at 30° C. overnight.

The culture broth of the strain was diluted at a ratio of 1:2,000 using 2 ml of analysis medium which was prepared by mixing the cell-free culture broth and MB with chloramphenicol at a ratio of 1:1(v/v). 2 ml of MB medium containing chloramphenicol was used as a control group. The transformant strains were cultured in the analysis medium and the control medium at 30° C. for 24 hours overnight. $OD_{600}$ value was measured using a spectrophotometer (SmartSpec 3000 spectrophotometer, Bio-Rad Laboratories, USA) to observe the growth of the strain.

Figure 1:
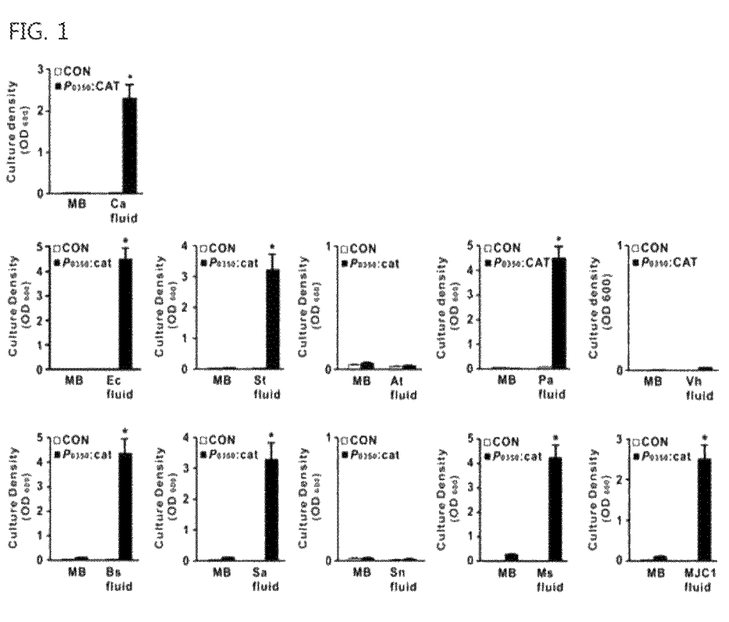
FIG. 1 shows the results of growth permissive assay for expression levels of the promoter of NCgI0350 gene (SEQ ID NO: 2) after treatment of cell-free culture broths obtained from Gram-negative or Gram-positive bacteria cultured to a stationary phase. The used Gram-negative bacteria were *Agrobacterium tumefaciens* (At), *Escherichia coil* (Ec), *Pseudomonas aeruginosa* (Pa), *Salmonella typhimurium* (St) and *Vibvrio harveyi* (Vh), and Gram-positive bacteria were *Bacillus subtilisBacillus subtilis* (Bs), *Corynebacterium ammoniagenes* (Ca), *Mycobacterium smegmatis* (Ms), *Mycobacterium* sp. strain JC1 (MJC1), *Staphylococcus aureus* (Sa) and *Bacillus subtilisStreptomyces natalensis* (Sn).

As shown in FIG. 1, the transformant strains did not grow in the MB medium containing chloramphenicol, whereas only C6(P0350:CAT) strain grew in the medium containing chloramphenicol, which was prepared by mixing the cell-free culture broth and MB medium at 1:1 ratio.

These results suggest that expression of the promoter of acyltransferase gene is induced in presence of the cell-free culture broths obtained from various bacteria, except *Agrobacterium tumefaciens Vibvrio harveyi*, and *Bacillus subtilisStreptomyces natalensis*.

EXAMPLE 2

Induction of Promoter Expression of Probable O-Antigen Acetylase (PA5238) Gene of *Pseudomonas aeruginosa* in Presence Cell-Free Culture Broths <2-1> Construction of Expression Vector Containing Promoter In Example 1, it was confirmed that the expression of the promoter of NCgI0350 gene increased in presence of the cell-free culture broth of *Pseudomonas aeruginosa*. Based on the result, to construct a screening system using *Pseudomonas aeruginosa*, a gene similar to NCgI0350 was screened in *Pseudomonas aeruginosa*. As a result, a probable O-antigen acetylase (PA5238) gene, represented by SEQ ID NO: 3 having 35% homology and 51% similarity, was selected.

Figure 2:
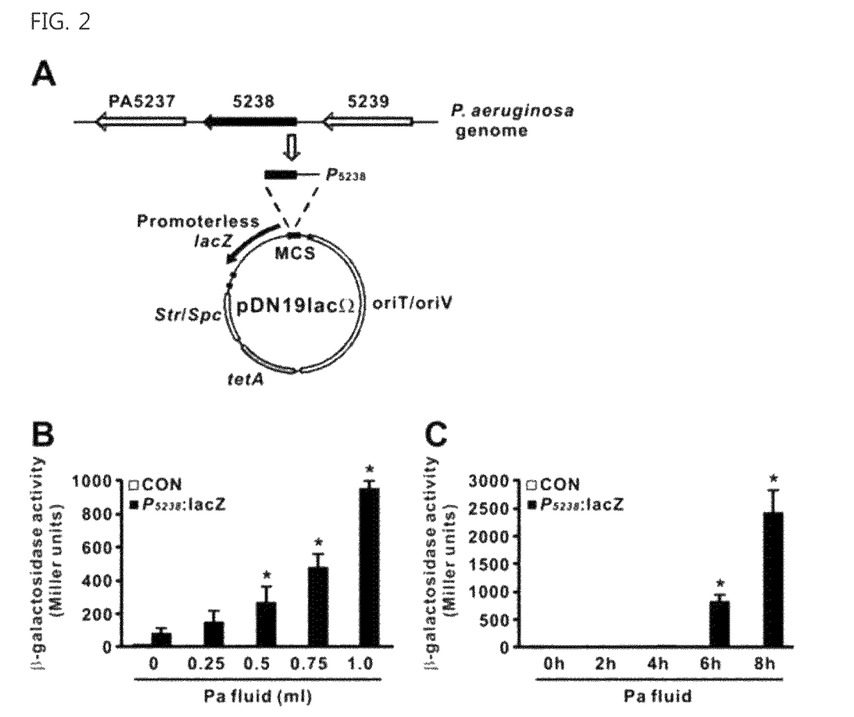

In order to examine expression of the PA5238 gene in presence of the cell-free culture broth, an expression vector of the promoter of PA5238 gene was constructed as shown in FIG. 2 panel A.

Figure 7:
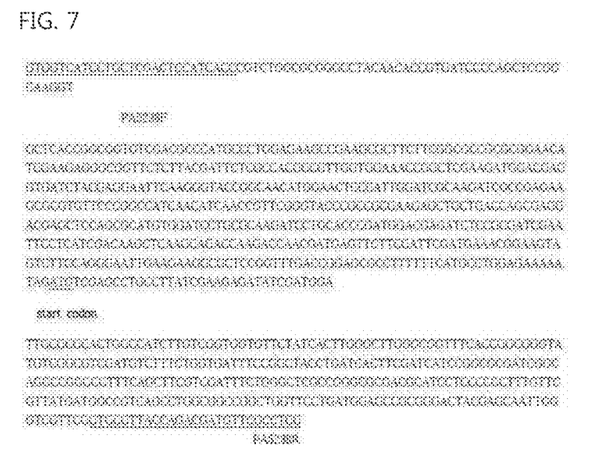
FIG. 7 shows primers and start codons used for cloning the promoter region of PA5238 of *Pseudomonas aeruginosa*.

More specifically, genomic DNA was isolated from *Pseudomonas aeruginosa* PAK, and then the promoter region of PA5238 represented by SEQ ID NO: 7 was amplified using a pair of PCR primers for cloning (5238F/5238R) as shown at Table 1 (FIG. 7).

TABLE 1

| Primer | Nucleotide sequence | SEQ ID NO: |
|---|---|---|
| PA5238F | 5'-GTGGTCATCCTGCTCGACTCCATCACC-3' | 5 |
| PA5238R | 5'-CGAGGCGAACATCGTCTGGTAACGCAC-3' | 6 |

The thus amplified promoter region was inserted into the T&A vector (Real Biotech Corporation), digested with KpnI, and then cloned into a pDP19lacΩ vector which was already digested with the same enzyme, to prepare a pHS1004 vector into which the promoter of PA5238 was inserted (FIG. 2 panel A).

The pDA19lacΩ vector used in the preparation of the pHS1004 vector is a promoterless vector including lacZ gene encoding β-galactosidase involved in color development with x-gal or ONPG ire *Pseudomonas aeruginosa* PAK.

<2-2> Induction of Promoter Expression of Probable O-Antigen Acetylase(PA5238) Gene in Presence of Cell-Free Culture Broths The pDN19lacΩ vector and the pHS1004 vector were transformed into the wild-type *Pseudomonas aeruginosa* PAK, respectively so as to prepare P19 and P18 (P5238:lacZ) transformants.

The P19 and P18 transformants were cultured in LM medium containing each 100 μg/ml of spectinomycin and streptomycin at 37° C. overnight, respectively.

The cell-free culture broth of *Pseudomonas aeruginosa* and LB medium were mixed at various ratio (v/v) as shown in FIG. 2 panel B to prepare 2 ml of analysis medium, then the analysis medium was used for incubation for 6 hours. More specifically, the cell-free culture broth and LB medium were mixed at a ratio of 0.25 ml:1.75 ml, 0.5 ml:1.5 ml 0.75 ml:1.25 ml, or 1.0 ml:1.0 ml so as to prepare each 2 ml of analysis medium. As a control group, 2 ml of LB medium was only used.

The transformant strains were mixed at a ratio of 1.0 ml:1.0 ml as in FIG. 2 panel C so as to prepare total 2 ml of analysis medium, and they were cultured in the analysis medium for different treatment times at 37° C.

Expression levels of β-galactosidase were examined by β-galactosidase assay using a spectrophotometer (Smart-Spec 3000 spectrophotometer, Bio-Rad Laboratories, USA).

As shown in FIG. 2 panel B, the expression levels did not increase in the control group whereas the P18(P5238:lacZ) strain showed an increase in β-galactosidase expression depending on the concentration of the cell-free culture broth of *Pseudomonas aeruginosa*.

Furthermore, it was confirmed that the β-galactosidase expression was increased in proportion to treatment time of the cell-free culture broth, and particularly, at least 6 hr-treatment time is required.

These results confirmed that expression of the promoter of the probable O-antigen acetylase (PA5238) gene can be induced in presence of the cell-free culture broth of *Pseudomonas aeruginosa*.

EXAMPLE 3

Induction of Promoter Expression of Probable O-Antigen Acetylase (PA5238) Gene of *Pseudomonas aeruginosa* in Presence Cell-Free Culture Broths Obtained from Various Bacteria Cell-free culture broths were prepared from various bacteria in the same manner as in <1-1> of Example and expression levels of β-galatosidase by the cell-free culture broths were examined by β-galactosidase assay described in <:2-2> of Example 2.

Figure 3:
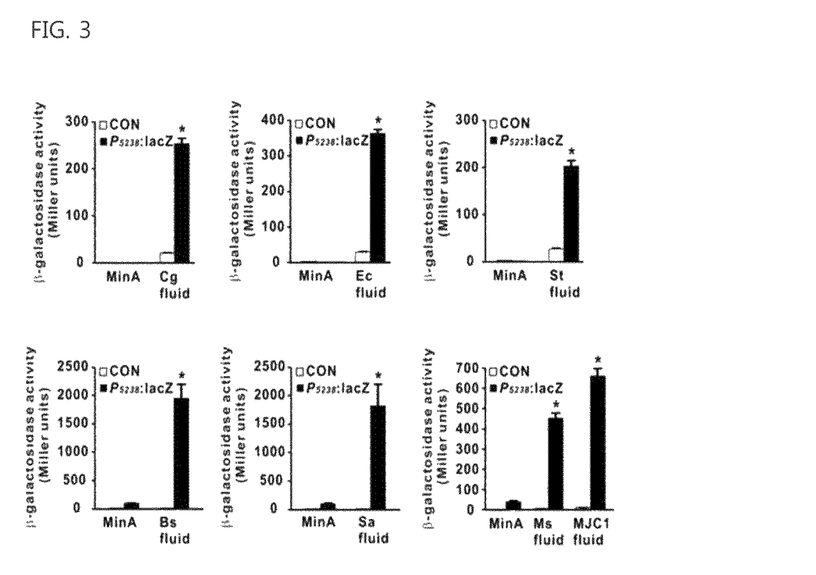
FIG. 3 shows that a promoter expression of PA5238 gene in *Pseudomonas aeruginosa* transduced with the pHS1004 vector was induced by using the cell-free culture broths obtained from bacteria cultured solutionin a stationary phase. The bacteria have induced promoter expression of NCgI0350 gene among the bacteria used in FIG. 1. The used Gram-negative bacteria were *Escherichia coli*(Ec), *Salmonella typhimurium*(St), and the used Gram-positive bacteria were *Bacillus subtilis* (Bs), *Corynebacterium glutamicum* (Cg), *Mycobacterium smegmatis*(Ms), *Mycobacterium* sp. strain JC1(MJC1) and *Staphylococcus aureus*(Sa).

Specifically, cell-free culture broths of *Corynebacterium glutamicum, Escherichia coli, Salmonella typhimurium, Bacillus subtilisBacillus subtilis, Staphylococcus aureus, Mycobacterium smegmatis* and *Mycobacterium* sp. strain JC1 were prepared in the same manner as in <1-1> of Example 1, and then expression levels of β-galactosidase were examined. It was confirmed that cell-free culture broths of various bacteria inducing expression of the promoter of the NCgI0350 gene of coryneform bacteria as in FIG. 1 also increased expression of the promoter of the PA5238 gene of *Pseudomonas aeruginosa*, as shown in FIG. 3.

EXAMPLE 4

Screening for Detecting Epistatic Regulatory Gene and Identification of Detected Gene <4-1> Screening for Detecting Epistatic Regulatory Gene PA5238 (SEQ ID NO: 3) of *Pseudomonas aeruginosa* identified in Example 3 and its promoter (SEQ ID NO: 7) were used to screen the epistatic gene related to its regulation. For screening, pBT20 (Molecular Microbiology 55(2): 368-380, 2005) having Mariner transposon was transformed into *Pseudomonas aeruginosa* having pHS1004 through conjugation.

In a transposon-inserted mutant pool, mutants showing no increase in the expression level despite treatment of the cell-free culture broth, thus appearing as white colonies in an x-gal-containing medium were detected. The transposon-inserted gene were analyzed via arbitrary PCR (Molecular Microbiology 55(2): 368-380, 2005) followed by sequencing.

From the genes analyzed, PA5309 (SEQ ID NO: 4) gene of *Pseudomonas aeruginosa* was found to have 22% homology and 39% similarity with NCgU2909 (SEQ ID NO: 1) of *Coryneform* bacteria in the amino add homology analysis.

<4-2> Preparation of Epistatic Regulatory Gene-Inactivated Strain

In order to prepare the NCgI2909 (SEQ ID NO: 1) gene-inactivated strain, pDZ which is not replicable in *Corynebacterium glutamicum* was used to prepare a pDZ derivative in which ORE of NCgI2909 was internally deleted.

In detail, based on NIH Genbank, the sequence of NCgI2909 (SEQ ID NO: 1) was obtained, and on the basis of this sequence, the primers 2909F1, 2909R1, 2909F2, and 2909R2 were prepared, respectively. Table 2 shows nucleotide sequence and SEQ ID NO: of the primers used in the present invention. The sequences underlined represent the recognition site for restriction enzyme.

TABLE 2

| Primer | Nucleotide sequence | SEQ ID NO: |
|---|---|---|
| 2909F1 | 5'-gctctagactctagcccaagcactc-3' | 8 |
| 2909R1 | 5'-acggccctcatacgg cacacgaagtggcatat-3' | 9 |
| 2909F2 | 5'-atgccacttcgtgtg ccgtatgagggccgttt-3' | 10 |
| 2909R2 | 5'-gctctagaaccttgtactgcgccga-3' | 11 | pDZ-ΔNCgI2909 includes 250 bp of the nucleotide sequence upstream of NCgI2909 and 140 bp of the nucleotide sequence downstream thereof, and primers containing the recognition site of the restriction enzyme XbaI at each end were prepared. Further, pDZ-ΔNCgI2909 includes internal gene deletion of NCgI2909, and the interna gene deletion of NCgI2909 was produced by crossover PCR using genomic DNA of *Corynebacterium glutamicum* ATCC13032 as a template and a pair of 2909F1-2909R1 primer (SEQ ID NOS: 8 and 9) and 2909F2-2909R2 primer (SEQ ID NOS: 10 and 11).

The recombinant plasmid was transformed into *Corynebacterium glutamicum* ATCC13032 by electroporation (van der Rest et al., Appl Microbiol Biotechnol 52:541.-545, 1.999), and the plasmid was incryrporated into the chromosome by primary recombination (crossover). Thereafter, the plasmid was excised from the chromosome by secondary recombination (crossover) on an agar plate containing 10% sucrose.

Using gene-specific primer pairs 2909F1-2909R2 (SEQ ID NOs. 8 and 11), PCR was performed on the *Corynebacterium glutamicum* transformants in which the secondary recombination was completed, thereby confirming deletion of the NCgI2909 gene. This recombinant strain was named as ATCC13032::ΔNCgI2909.

<4-3> Effect of Epistatic Regulatory Gene

The effect on induction of NCgI0350 promoter expression was examined using the prepared strain by the growth permissive assay described in <1-2> of Example 1. The C3 and C6(P0350:CAT) strains, prepared by transformation of the wild-type *Corynebacterium glutamicum* ATCC13032 with each of pSK1CAT vector and pHS09004 vector, and the ATCC13032::ΔNCgI2909(P0350:CAT) strain, prepared by transformation of ATCC13032::ΔNCgI2909 with the pHS09004 vector, were compared.

Figure 4:
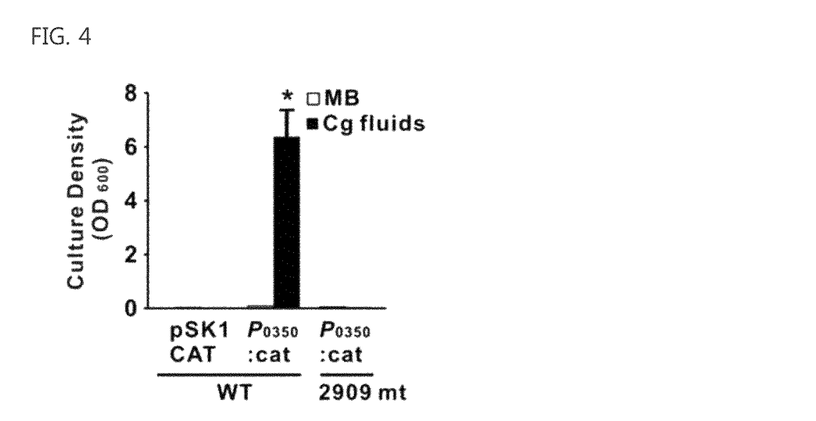
FIG. 4 shows the results of growth permissive assay for the promoter expression of NCgI0350 gene in a *Corynebacterium glutamicum* (Cg) wild-type strain and a NCgI2909 gene-inactivated strain prepared therefrom.

The cell-free culture broth obtained from *Corynebacterium glutamicum* was used to examine whether expression of the promoter of the NCgI0350 gene is induced. As a shown in FIG. 4, the promoter expression was induced in the C6(P0350:CAT) transformant strain, and thus the strain grew in the medium containing chloramphenicol, whereas ATCC13032::ΔNCgI2909(P0350:CAT) strain did not grow. These results suggest that the NCgI2909 gene is involved in induction of the NCgI0350 gene expression in the presence of the cell-free culture broth.

EXAMPLE 5

Effect of NCgI2909 on Biofilm Formation

Biofilm formation of the wild-type *Corynebacterium glutamicum* and *Corynebacterium glutamicum* ATCC13032::ΔNCgI2909 prepared in Example 4 was compared. Biofilm formed on a 96 well-microtiter plate made of PVC (polyvinylchloride plastics) was examined using the method of Fletcher (Can. J. Microbiol, 23:1-6, 1977). In more detail, the strains were cultured in MB medium at 30° C. overnight, and the cultured strains were diluted at a ratio of 1:100, and 200 μl of each diluted strain was inoculated into each well of the 95-well microtiter plate. The plate was incubated at 30° C. for 1~2 days, and then washed with 200 μl of distilled water three times. 200 μl of 0.3% crystal violet was added to each well. Thereafter, the plate was incubated at room temperature for 30 minutes, and washed with 200 μl of distilled water three times. The plate was dried at room temperature for 10 minutes, and 200 μl of 95% ethanol was added to each well stained with crystal violet for quantification. The plate was incubated at room temperature for 20 minutes, and absorbance at 540 nm was measured.

Figure 5:
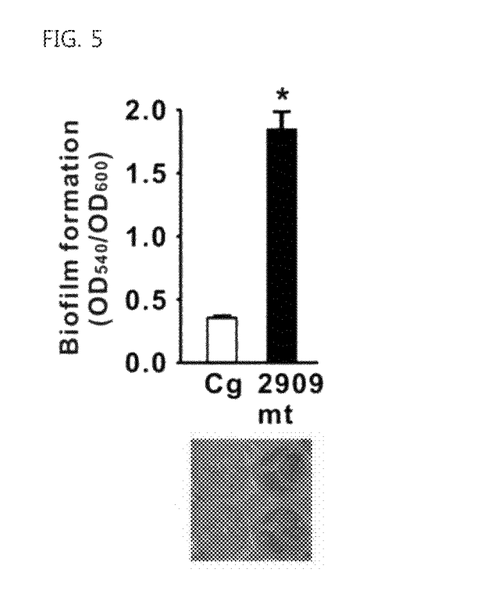
FIG. 5 shows the level of biofilm formation in a NCgI2909 mutant strain and the wild-type *Corynebacterium glutamicum* strain.
Figure 6:
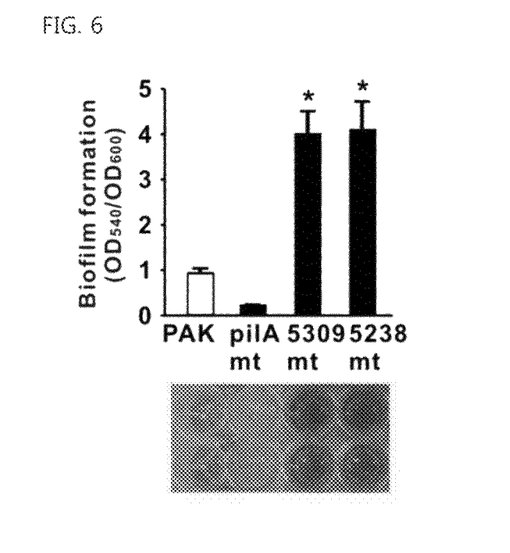
FIG. 6 shows the level of biofilm formation of a mutant strain of *Pseudomonas aeruginosa* PA5309 having homology with *Corynebacterium glutamicum* NCgI2909 and a mutant strain of *Pseudomonas aeruginosa* PA5238 gene having homology with *Corynebacterium glutamicum* NCgI0350 gene, which was compared with those of the wild-type strain and a negative control group (pilA mutant strain).

As shown in FIG. 5, ATCC13032::ΔNCgI2909 showed approximately 4~5-fold higher biofilm formation than the wild-type.

EXAMPLE 6

Effect of Inactivated Biofilm Inhibition Gene on L-lysine Producibility

<6-1> Preparation of a Lysine-Producing Strain Having Inactivated Biofilm Inhibition Gene A Lysine-producing strain was used to prepare strains having inactivated NCgI2909 or NCgI0350, or inactivated NCgI2909 and NCgI0350, and the effect of the inactivated biofilm inhibition gene on L-lysine producibility was examined in these strains.

To prepare NCgI2909 gene-deleted recombinant strains, a recombinant plasmid pDZ-ΔNCgI2909 described in <4-2> of Example 4 was used. pDZ-ΔNCgI2909 was introduced into a lysine-producing strain, *Corynebacterium glutamicum* KCCM11016P so as to select a transformed strain. This strain was named as KCCM11016P::ΔNCgI2909.

To prepare NCgI0350 (SEQ ID NO: 2) gene inactivated strains, a pDZ derivative in which ORF of NCgI0350 was internally deleted was prepared using the method described in <4-2> of Example 4. The derivative is pDZ-ΔNCgI0350 (FIG. 9). Table 3 shows nucleotide sequence and SEQ ID NOS of the primers used in the present invention.

TABLE 3

| Primer | Nucleotide sequence | SEQ ID NO: |
|---|---|---|
| 0350F1 | 5'-cgactctagattaggtcttagttgccatgatcggt-3' | 12 |

TABLE 3-continued

| Primer | Nucleotide sequence | SEQ ID NO: |
|---|---|---|
| 0350R1 | 5'-tgcacctaatgttgg ccatcgccagcatgaaat-3' | 13 |
| 0350F2 | 5'-tcatgctggcgatgg ccaacattaggtgcagca-3' | 14 |
| 0350R2 | 5'-atctctagagcagcttggcttctatttggagat-3' | 15 |

The recombinant plasmid pDZ-ΔNCgI0350 was introduced into *Corynebacterium glutamicum* KCCM11016P to prepare a transformed strain, which was named as KCCM11016P::ΔNCgI0350.

Further, to prepare an NCgI2909 and NCgI0350-inactivated strain, the recombinant plasmid pDZ-ΔNCgI0350 was introduced into KCCM11016P::ΔNCgI2909 in the same manner as above, so as to prepare an NCgI2909 and NCgI0350-inactivated strain. The strain was named as CA01-2270 (KCCM11016P::ΔNCgI2909ΔNCgI0350) and deposited on Jun. 12, 2013 at the Korean Culture Center of Microorganisms under accession number KCCM11431P.

<6-2> L-lysine Producibility of Strain Having Inactivated Biofilm Inhibition Gene The L-lysine-producing *Corynebacterium glutamicum* strains, KCCM11016P::ΔNCgI2909, KCCM11016P::ΔNCgI0350 and CA01-2270 were cultured for L-lysine production as follows.

The parent strain *Corynebacterium glutamicum* KCCM11016P and the above three types of recombinant strains were respectively inoculated in 250 ml corner-baffled flasks containing 25 ml of the seed medium described below, and cultured at 30° C. with shaking at 200 rpm for 20 hours. 1 mL of the resulting seed culture broth was inoculated to a 250 ml corner-baffled flask containing 24 ml of the production medium described below, and cultured at 30° C. with shaking (200 rpm) for 120 hours. The compositions of the seed medium and the production medium are the same as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4$ $7H_2O$, 100 μg of biotin, 1000 μg of thiamine-HCl, 2000 μg of calcium-pantothenate, 2000 μg of nicotine amide (in 1 liter of distilled water)

<Production Medium (pH 7.0)>

100 g of glucose, 40 g of $(NH_4)_2SO_4$, 2.5 g of soybean protein, 5 g of corn steep solids, 3 g of urea, 1 g of $KH_2PO_4$, 0.5 g of $MgSO_4$ $7H_2O$, 100 μg of biotin, 1000 μg of Thiamine-HCl, 2000 μg of calcium-pantothenate, 3000 μg of nicotine amide, 30 g of $CaCO_3$ (in 1 liter of distilled water)

After completing the culture, the quantity of produced L-lysine was measured by HPLC. Besides, the cell mass and L-lysine concentration in the culture broths of *Corynebacterium glutamicum* KCCM.11016P, and KCCM11016P::ΔNCgI2909, KCCM11016P::ΔNCgI0350 and CA01-2270 are shown in the following Table 4.

TABLE 4

| | Cell mass (OD562) | | | L-lysine (g/l) | | |
|---|---|---|---|---|---|---|
| Strain | batch 1 | batch 2 | batch 3 | batch 1 | batch 2 | batch 3 |
| KCCM11016P | 45.5 | 50.6 | 51.3 | 42.9 | 41.2 | 42.3 |
| KCCM11016P::ΔNCgI2909 | 61.4 | 62.4 | 59.8 | 43.2 | 42.3 | 40.2 |
| KCCM11016P::ΔNCgI0350 | 57.2 | 59.6 | 58.7 | 42.7 | 41.5 | 42.5 |
| CA01-2270 | 64.2 | 66.0 | 65.4 | 43.0 | 41.6 | 42.0 |

As shown in Table 4, when ΔNCgI2909 gene or ΔNCgI0350 gene was inactivated in the parent strain KCCM111016P, the cell mass was increased to 24% or 1.9% respectively, compared with the parent strain. CA01-2270 strain, in which both ΔNCgI2909 gene and ΔNCgI0350 gene were inactivated, showed 33% increase in the cell mass, In contrast, all of the three strains showed the L-lysine productivity equivalent to the parent strain (Table 4). These results indicate that cell mass can be increased by inactivation of the NCgI2909 and/or NCgI0350 genes, and L-lysine yield isn't decreased even though increasing cell mass. Consequently, it is possible to produce L-lysine in a higher yield with increasing cell mass.

<6-3> Effect in Different L-lysine-Producing Strains

Based on the above results, NCgI2909 and NCgI0350 gene-inactivated strains were prepared using three different types of strains other than a L-lysine-producing strain *Corynebacterium glutamicum* KCCM11016P. Then, it was examined whether the same effects were found in the strains.

NCgI2909 and NCgI0350 gene-inactivated strains were prepared by the method described in <6-1>. Three types of strains in which the two genes were inactivated were prepared using three different types of lysine-producing strains, *Corynebacterium glutamicum* KCCM10770P, KFCC17050 (Accession No. KCCM1137P) and CJ3P strain. The strains were named as KCCM10770P::ΔNCgI2909ΔNCgI0350, KFCC10750::ΔNCgI2909ΔNCgI0350, and CJ3P::ΔNCgI2909ΔNCgI0350, respectively.

The three types of strains and the parent strains thereof were cultured in the same manner as in <6-2>, and the cell mass and L-lysine concentration in the culture broths were measured, and shown in the following Table 5.

TABLE 5

| | Cell mass (OD562) | | | L-lysine (g/l) | | |
|---|---|---|---|---|---|---|
| Strain | Batch 1 | Batch 2 | Batch 3 | Batch 1 | Batch 2 | Batch 3 |
| KCCM10770P | 50.1 | 55.7 | 48.4 | 47.5 | 46.9 | 46.5 |
| KCCM10770P::ΔNCgI2909ΔNCgI0350 | 63.0 | 62.0 | 57.3 | 45.6 | 46.6 | 46.8 |
| KFCC10750 | 55.5 | 57.0 | 58.4 | 37.5 | 38.2 | 37.4 |
| KFCC10750::ΔNCgI2909ΔNCgI0350 | 66.9 | 63.8 | 65.8 | 38.9 | 38.4 | 37.5 |
| CJ3P | 75.5 | 80.4 | 78.5 | 7.8 | 8.2 | 8.1 |
| CJ3P::ΔNCgI2909ΔNCgI0350 | 85.5 | 90.1 | 92.1 | 7.5 | 7.9 | 8.0 |

As shown in Table 5, the cell mass was increased in each culture broth of three types of strains which were transformed from the respective parent strains. KCCM10770P::ΔNCgI2909ΔNCgI0350, KFCC10750::ΔNCgI2909ΔNCgI0350 or CJ3P::ΔNCgI2909ΔNCgI0350 showed 18%, 15%, or 14% increase in cell mass, respectively. However, they showed L-lysine productivity equivalent to the parent strain.

The NCgI2909 and NCgI0350 inactivated strains prepared from three different types of parent strains showed the same phenotype in the cell mass and L-lysine productivity, demonstrating the effect of NCgI2909 and NCgI0350 gene on L-lysine producibilty.

Effect of the Invention

The NCgI2909 gene of the present invention having a biofilm formation-inhibitory activity is not unique that particular bacteria only has, and its expression is induced in presence of cell-free culture broths obtained from Gram-negative or Gram-positive bacteria which are cultured until stationary phase. The induction of the expression has an inhibitory effect on biofilm formation.

Further, a L-lysine-producing strain in which the NCgI2909 gene having a biofilm formation-inhibitory activity is inactivated shows no reduction in L-lysine productivity even though its mass is increased.

Therefore, L-lysine can be produced with a high yield in a short period of time by using the L-lysine-producing strain in which the NCgI2909 or NCgI0350 gene, or both NCgI2909 and NCgI0350 gene(s) encoding a biofilm formation-inhibitory activity is/are inactivated.

What is claimed is:

1. *Corynebacterium glutamicum* wherein a gene with a nucleotide sequence as set forth in SEQ ID NO: 1 is inactivated.

2. *Corynebacterium glutamicum* wherein a gene with a nucleotide sequence as set forth in SEQ ID NO: 2 is inactivated.

3. *Corynebacterium glutamicum* wherein genes with nucleotide sequences as set forth in SEQ ID NOs. 1 and 2 are inactivated.

4. A method for producing L-lysine comprising, culturing *Corynebacterium glutamicum* in a culture solution, in which a gene with a nucleotide sequence as set forth in SEQ ID NO: 1 is inactivated; and recovering lysine from the cultured bacteria or the culture solution thereof.

5. A method for producing L-lysine comprising, culturing *Corynebacterium glutamicum* in a culture solution, in which a gene with a nucleotide sequence as set forth in SEQ ID NO: 2 is inactivated; and recovering lysine from the cultured bacteria or the culture solution thereof.

6. A method for producing L-lysine comprising culturing *Corynebacterium glutamicum* in a culture solution, in which genes of nucleotide sequences as sey forth in SEQ ID NOS: 1 and 2 are inactivated; and recovering lysine from the cultured bacteria or the culture solution thereof.

* * * * *